United States Patent [19]

Sakata et al.

[11] 4,425,343

[45] Jan. 10, 1984

[54] BENZOAZINE ETHER OR THIOETHER LINKAGE CONTAINING UREA COMPOUNDS, PROCESS FOR PRODUCING SAME AND INSECTICIDES CONTAINING SAID COMPOUNDS

[75] Inventors: Gojyo Sakata; Kenji Makino; Yasuo Kawamura; Jun Sato; Kiyomi Ozawa, all of Funabashi; Masayoshi Hirose; Kiminori Hirata, both of Saitama, all of Japan

[73] Assignee: Nissan Chemical Industries, Ltd., Tokyo, Japan

[21] Appl. No.: 267,077

[22] Filed: May 26, 1981

[30] Foreign Application Priority Data

Oct. 24, 1980 [JP] Japan .................... 55-149015
Mar. 30, 1981 [JP] Japan .................... 56-46851

[51] Int. Cl.³ .............. C07D 241/44; C07D 215/22; A61K 31/495; A61K 31/47
[52] U.S. Cl. .................... 424/250; 546/157; 544/354; 424/258
[58] Field of Search .............. 546/157; 544/354; 424/250, 258

[56] References Cited

U.S. PATENT DOCUMENTS 4,133,956  1/1979  Abdulla .................... 544/356
4,173,637  11/1979 Nishiyama et al. ........... 424/263
4,173,638  11/1979 Nishiyama et al. ........... 424/263

FOREIGN PATENT DOCUMENTS 53-56670  5/1978  Japan .
54-106475 8/1979  Japan .
54-125677 9/1979  Japan .
55-38356  3/1980  Japan .
55-79369  6/1980  Japan .
55-98153  9/1980  Japan .

OTHER PUBLICATIONS

Kaisha, Chem. Abs. 94, 208901t (2-14-81).

Primary Examiner—Mark L. Berch
Attorney, Agent, or Firm—Parkhurst & Oliff

[57] ABSTRACT

This invention relates to a heterocyclic ether or thioether linkage containing urea compounds of the following formula I:

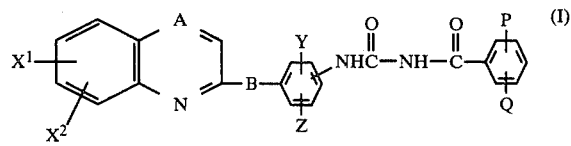

wherein B denotes an oxygen atom or a sulfur atom, A denotes CH or a nitrogen atom, $X^1$ and $X^2$ denote independently of each other hydrogen atom, halogen atom, trifluoromethyl group or nitro group, Y and Z denote independently of each other hydrogen atom or halogen atom, and P and Q denote independently of each other hydrogen atom, halogen atom, alkoxyl group or alkyl group, a process for producing the same and an insecticide containing the same.

20 Claims, No Drawings

BENZOAZINE ETHER OR THIOETHER LINKAGE CONTAINING UREA COMPOUNDS, PROCESS FOR PRODUCING SAME AND INSECTICIDES CONTAINING SAID COMPOUNDS

BACKGROUND OF THE INVENTION

This invention relates to a novel heterocyclic ether or thioether linkage containing urea compounds, a process for producing the same and an insecticides containing the same.

A variety of insecticides have been put to practical use by years of research and development of insecticides, and these insecticides have contributed to improvement of the productivity of agricultural and horticultural product.

However, there is still a need to develop novel insecticides having more excellent insecticidal properties.

Concerning heterocyclic ether or thioether linkage containing urea compounds, Japanese Patent Application Laid-Open No. 106475/1979 describes that substituted ether linkage containing urea compounds can be used as insecticides. Also, Japanese Patent Application Laid-Open No. 98153/1980 describes naphthyl ether linkage containing urea compounds and insecticidal action thereof.

The heterocyclic ether or thioether linkage containing urea compounds having a quinoline or quinoxaline skeleton, however, are novel compounds which have not been described in literature. After strenuous effort in developing novel and useful insecticides, the present inventors have newly found such compounds.

SUMMARY OF THE INVENTION

An object of this invention is to provide novel heterocyclic ether or thioether linkage containing urea compounds having an excellent insecticidal activity.

Another object of this invention is to provide insecticides containing a novel heterocyclic ether or thioether linkage containing urea compound as an active ingredient.

Still another object of this invention is to provide a process for producing novel heterocyclic ether or thioether linkage containing urea compounds.

These and other objects of this invention will be more apparent from the following detailed description and examples.

DETAILED DESCRIPTION

The novel compound of this invention is represented by the following formula I:

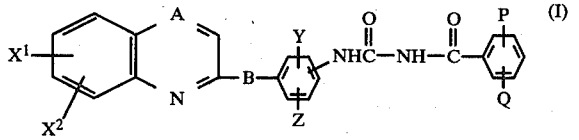

wherein B denotes an oxygen atom or a sulfur atom, A denotes CH or a nitrogen atom, $X^1$ and $X^2$ denote independently of each other hydrogen atom, halogen atom, trifluoromethyl group or nitro group, Y and Z denote independently of each other, hydrogen atom or halogen atom, and P and Q denote independently of each other hydrogen atom, halogen atoms, alkoxyl groups or alkyl groups.

In general, the compounds of this invention can be prepared according to a method represented by the following reaction formula:

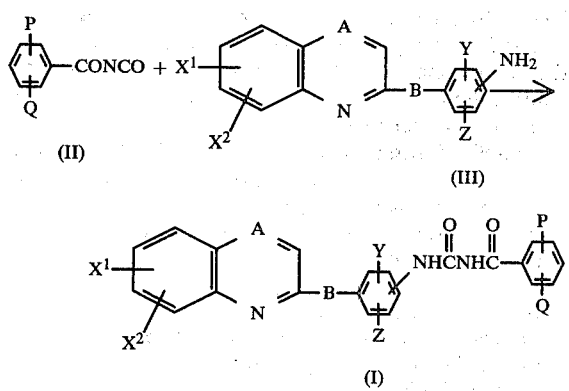

wherein B, A, $X^1$, $X^2$, Y, Z, P and Q have the same meanings as above.

Namely, the compounds of this invention can be prepared by condensing a benzoyl isocyanate represented by the general formula II with an aniline derivative represented by the general formula III, preferably in the presence of an inert solvent to the reactants.

As the reaction solvent, there is used a solvent such as benzene, toluene, acetonitrile or pyridine.

The reaction temperature and time may vary according to starting materials, and usually, a reaction temperature ranging from $-20°$ C. to $100°$ C. and a reaction time ranging from 0.5 hour to 24 hours are preferred.

The compound of the formula III can be prepared as follows:

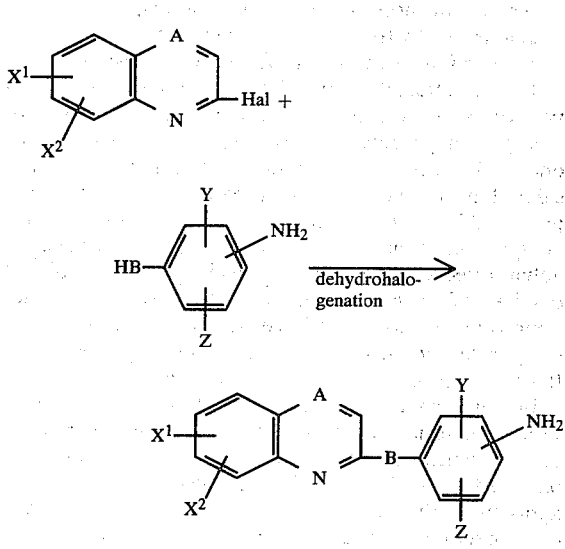

wherein B, A, $X^1$, $X^2$, Y, Z denote the same meanings given in the formula I.

The thus-prepared compounds of this invention are compounds which are extremely useful as agents for controlling and combating sanitary insect pests as well as insect pests of forest, insect pests in stored corps and agricultural and horticultural insect pests which damage paddy-rice plants, vegetables, fruit trees, cotton plants and other crops and flowering plants.

According to this invention, there are provided insecticides which are used to sprinkle an effective amount of the compound of this invention together with a suitable carrier over habitats of insect pests.

Habitats of insect pests mean any areas where insects live, including soil, air, water, foods, plants, fertilizers, inert substances and stored products such as crops.

The following are examples of insect pests to which the compounds of this invention are applicable. Of course, these examples are non-limitative.

Sanitary insect pests:
housefly (*Musca domestica*), mosquito (Culex spp., Aedes spp., Anopheles spp.) cockroach (Periplaneta spp., Blatella spp.)

Agricultural and horticultural insect pests:
(Insect pests of rice)
rice stem borer (*Chilo suppressalis*),
rice leaf beetle (*Oulema oryzae*),
ricewater weevil (*Lissothoptrus oryzophilus*),
rice leaf miner (*Agromyza oryzae*),
smaller rice liaf miner (*Hydrellia griseola*),
small brown planthopper (*Laodelphax striatella*),
white-backed planthopper (*Sogatella furcifera*),
brown planthopper (*Nilaparvata lugens*),
green rice leafhopper (*Nephotettix cincticeps*)
(Vegetable insect pests)
cabbage armyworm (*Mamestra brassicae*),
tobacco cutworm (*Spodoptera litura*),
common white (*Pieris rapae crucivora*),
diamondback moth (*Plutella xylostella*),
28-spotted lady bettle (*Epilachna vigintioctopunctata*),
Green peach aphid (*Myzus persicae*)
(Insect pest of tree fruit)
tortrix, Leafrolles (Adoxophyes spp., Archeps spp., Archi ppus spp.),
apple leafminer (*Phyllonorycter ringoneella*),
oriental fruit moth (*Grapholita molesta*),
peach fruit moth (*Carposina niponensis*),
smaller tea tortrix (*Adoxophyes orana*),
comstock mealybug (*Pseudococcus comstocki*)

The insecticidal action of the compounds of this invention is considered to consist in the disturbance of metamorphic mechanisms of insect pests, with consequent kills of them. For producing this action, it is considered necessary that insect pests take in the compound. Although, in certain insect pests, their deaths postpone until they enter the metamorphosis stages, the actual effects of this activity result in the control and combat of them. Insecticides comprising the compounds of this invention have effectiveness also against early instar larvae and late instar larvae, and their effectiveness appears directly or systemically.

In applying the insecticides of this invention, it is preferable to use the agent usually in an active ingredient concentration of 0.1-10,000 ppm, and preferably 0.5-2,000 ppm. In case of insect pests living in water, applying of the agent in the above concentration range over breeding areas can control the insects, and therefore, concentrations in the water outside the above range are also effective.

When the compounds of this invention are used as an insecticides, the compounds are applied in admixture with a suitable carrier, e.g., a solid carrier such as clay, talc or bentonite, or a liquid carrier such as water, alcohol (methanol or ethanol), a ketone, an ether, aliphatic hydrocarbons, aromatic hydrocarbons (benzene, toluene or xylene) an organic base, acid amide (dimethylformamide), esters or nitriles in the dissolved, dispersed, suspended, blended, immersed, adsorbed or adhered state. If necessary, the insecticides of this invention can contain an emulsifier, a dispersant, a suspending agent, a spreader, a penetrant or a stabilizer, and can be used in any form of emulsions, oils, wettable powders, dusts, granules, tablets, pastes, flowables, aerosols, fumigant, mosquito, incense stick or electric mosquito mat.

Also, if desired, at the time of formulation or application, the insecticides of this invention can be mixed or simultaneously applied with different insecticides, various germicides, herbicides, plant-controlling agent and fertilizers.

Still higher insecticidal action can be obtained by adding to the compounds of this invention, a synergist such as piperonyl butoxide, octachlorodipropyl ether or N-octylbicycloheptane dicarboximide.

Also, the stability of the compounds of this invention can be increased by adding thereto as an antioxidant, a phenolic compound such as 2,6-di-tert-butyl-4-methylphenol or 2,6-di-tert-butylphenol or other amines.

This invention is illustrated in further detail below with reference to examples, formulations and tests, but not limited thereto.

EXAMPLE 1

Preparation of N-(2,6-dichlorobenzoyl)-N'-4-(2-quinolyloxy)phenyl urea (compound No. 30) represented by the following formula:

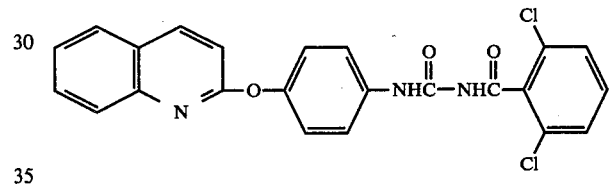

To a solution of 1.2 g ($5.0 \times 10^{-3}$ mol) of 4-(2-quinolyloxy)aniline in 40 ml of acetonitrile was added dropwise with stirring at 0° C., 1.0 g ($4.6 \times 10^{-3}$ mol) of 2,6-dichlorobenzoyl isocyanate. The reaction mixture was allowed to react overnight at room temperature, and the crystal formed was filtered off, washed with acetonitrile and dried to yield 1.5 g of the desired compound (compound No. 30) as a white crystal, m.p. 234°–235.5° C.

EXAMPLE 2

Preparation of N-(2,6-dimethoxybenzoyl)-N'[-3-chloro-4-(6-fluoro-2-quinoxalyloxy)phenyl]urea (compound No. 38) represented by the following formula:

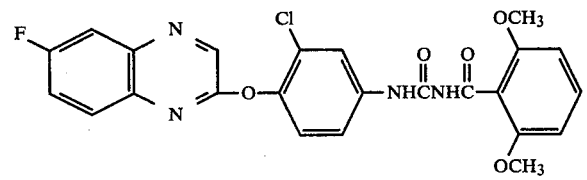

To a solution of 0.87 g ($3.0 \times 10^{-3}$ mol) of 3-chloro-4-(6-fluoro-2-quinoxalyloxy)aniline in 30 ml of acetonitrile was added dropwise with stirring at 0° C., 0.6 g ($2.9 \times 10^{-3}$ mol) of 2,6-dimethoxybenzoyl isocyanate. The reaction mixture was allowed to react overnight at room temperature, and the crystal formed was filtered off, washed with acetonitrile and dried to yield 1.0 g of the desired compound (compound No. 38) as a white crystal, m.p. 227°–229° C.

EXAMPLE 3

Preparation of N-(2-chlorobenzoyl)-N'-[4-(6-chloro-2-quinoxalyloxy)phenyl]urea (compound No. 10) represented by the following formula:

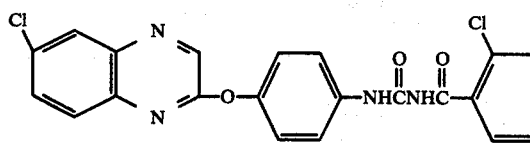

To a solution of 1.1 g (4.0×10$^{-3}$ mol) of 4-(6-chloro-2-quinoxalyloxy)aniline in 40 ml of acetonitrile was added dropwise with stirring at 0° C., 0.7 g (3.9×10$^{-3}$ mol) of 2-chlorobenzoyl isocyanate. The reaction mixture was allowed to react overnight at room temperature, and the crystal formed was filtered off, washed with acetonitrile and dried to yield 1.1 g of the desired compound (compound No. 10) as a white crystal, m.p. 238°–240° C.

In the same manner as in the above examples, compounds listed in the following tables 1 and 2 were prepared. Preparation of compounds represented by the following formula Ia:

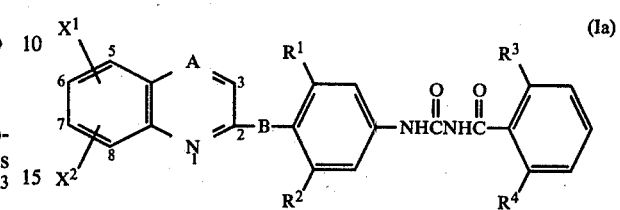

TABLE 1

| Compound No. | A | B | X$^1$ | X$^2$ | R$^1$ | R$^2$ | R$^3$ | R$^4$ | Properties | m.p. (°C.) |
|---|---|---|---|---|---|---|---|---|---|---|
| 1 | N | O | H | H | H | H | F | F | white crystal | 218–219 |
| 2 | N | O | H | H | H | H | Cl | H | white crystal | 241–242 |
| 3 | N | O | H | H | H | H | Cl | Cl | white crystal | 228–230 |
| 4 | N | O | H | H | Cl | Cl | F | F | white crystal | 215–217 |
| 5 | N | O | H | H | Cl | Cl | Cl | H | white crystal | 205–207 |
| 6 | N | O | H | H | Cl | Cl | Cl | Cl | white crystal | 251–253 |
| 7 | N | S | H | H | H | H | Cl | Cl | white crystal | 222–224 |
| 8 | N | S | H | H | H | H | F | F | white crystal | 224–226 |
| 9 | N | O | 6-Cl | H | H | H | F | F | white crystal | 227–228 |
| 11 | N | O | 6-Cl | H | H | H | Cl | Cl | white crystal | 225–226 |
| 12 | N | O | 6-Cl | H | Cl | H | F | F | white crystal | 236–238 |
| 13 | N | O | 6-Cl | H | Cl | H | Cl | H | white crystal | 227–228 |
| 14 | N | O | 6-Cl | H | Cl | H | Cl | Cl | white crystal | 239–240 |
| 15 | N | O | 6-Cl | H | Cl | Cl | F | F | white crystal | 229–230 |
| 16 | N | O | 6-Cl | H | Cl | Cl | Cl | H | white crystal | 244–246 |
| 17 | N | O | 6-Cl | H | Cl | Cl | Cl | Cl | white crystal | 255–256 |
| 18 | N | S | 6-Cl | H | H | H | F | F | white crystal | 236–239 |
| 19 | N | O | 6-F | H | H | H | Cl | H | white crystal | 238–239 |
| 20 | N | O | 6-F | H | Cl | H | F | F | white crystal | 227–230 |
| 21 | N | O | 6-F | H | Cl | H | Cl | H | white crystal | 227–231 |
| 22 | N | O | 6-F | H | Cl | H | Cl | Cl | white crystal | 245–246 |
| 23 | N | O | 6-F | H | Cl | Cl | F | F | white crystal | 222–225 |
| 24 | N | O | 6-F | H | Cl | Cl | Cl | H | white crystal | 224–225 |
| 25 | N | O | 6-F | H | Cl | Cl | Cl | Cl | white crystal | 241–244 |
| 26 | N | O | 6-NO$_2$ | H | Cl | Cl | F | F | white crystal | 275° C. - decomp. |
| 27 | N | O | 6-NO$_2$ | H | Cl | Cl | Cl | H | white crystal | 257–260 |
| 28 | N | O | 6-NO$_2$ | H | Cl | Cl | Cl | Cl | white crystal | 285° C. - decomp. |
| 29 | N | O | 6-CF$_3$ | H | Cl | H | Cl | H | white crystal | 207–210 |
| 31 | CH | O | H | H | Cl | H | F | F | white crystal | 199–201 |
| 32 | CH | O | H | H | Cl | H | Cl | H | white crystal | 219–221 |
| 33 | CH | O | H | H | Cl | H | Cl | Cl | white crystal | 246–247 |
| 34 | CH | O | 3-Cl | 6-Cl | H | H | Cl | Cl | white crystal | above 260 |
| 35 | N | O | H | H | Cl | Cl | OCH$_3$ | OCH$_3$ | white crystal | 238–242 |
| 36 | N | O | H | H | H | H | F | Cl | white crystal | 220–222 |
| 37 | N | O | H | H | H | H | OCH$_3$ | OCH$_3$ | white crystal | 223–226 |
| 38 | N | O | H | H | Cl | Cl | F | Cl | white crystal | 238–240 |
| 39 | N | S | H | H | H | H | F | Cl | white crystal | 199–201 |
| 40 | N | S | H | H | H | H | Cl | Cl | white crystal | 217–220 |
| 41 | N | S | H | H | H | H | OCH$_3$ | OCH$_3$ | white crystal | 236–239 |
| 42 | N | O | 6-Cl | H | H | H | OCH$_3$ | OCH$_3$ | white crystal | 233–236 |
| 43 | N | O | 6-Cl | H | Cl | H | F | Cl | white crystal | 120–121 |
| 44 | N | O | 6-Cl | H | Cl | H | OCH$_3$ | OCH$_3$ | white crystal | 242–244 |
| 45 | N | O | 6-Cl | H | Cl | Cl | F | Cl | white crystal | 217–219 |
| 46 | N | O | 6-Cl | H | Cl | Cl | OCH$_3$ | OCH$_3$ | white crystal | 272 |
| 47 | N | S | 6-Cl | H | H | H | Cl | H | white crystal | 220–223 |
| 48 | N | S | 6-Cl | H | H | H | Cl | Cl | white crystal | 208–210 |
| 49 | N | S | 6-Cl | H | H | H | OCH$_3$ | OCH$_3$ | white crystal | 216–220 |
| 50 | N | O | 6-F | H | H | H | F | F | white crystal | 235–238 |
| 51 | N | O | 6-F | H | H | H | F | Cl | white crystal | 220–222 |
| 52 | N | O | 6-F | H | H | H | Cl | Cl | white crystal | 238–241 |
| 53 | N | O | 6-F | H | H | H | OCH$_3$ | OCH$_3$ | white crystal | 229–233 |
| 54 | N | O | 6-F | H | Cl | H | F | Cl | white crystal | 225–227 |
| 55 | N | O | 6-F | H | Cl | Cl | F | Cl | white crystal | 220–221 |
| 56 | N | O | 6-F | H | Cl | Cl | OCH$_3$ | OCH$_3$ | white crystal | 250–251 |
| 57 | N | O | 6-Cl | 7-Cl | Cl | Cl | F | F | white crystal | above 300 |
| 58 | N | O | 6-Cl | 7-Cl | Cl | Cl | F | Cl | white crystal | above 300 |
| 59 | N | O | 6-Cl | 7-Cl | Cl | Cl | Cl | H | white crystal | above 300 |
| 60 | N | O | 6-Cl | 7-Cl | Cl | Cl | Cl | Cl | white crystal | above 300 |

TABLE 1-continued

| Compound No. | A | B | $X^1$ | $X^2$ | $R^1$ | $R^2$ | $R^3$ | $R^4$ | Properties | m.p. (°C.) |
|---|---|---|---|---|---|---|---|---|---|---|
| 61 | N | O | 6-Cl | 7-Cl | Cl | Cl | $OCH_3$ | $OCH_3$ | white crystal | above 300 |
| 62 | N | O | 6-$CF_3$ | H | Cl | Cl | F | F | white crystal | 240–243 |
| 63 | N | O | 6-$CF_3$ | H | Cl | Cl | F | Cl | white crystal | 240–243 |
| 64 | N | O | 6-$NO_2$ | H | Cl | Cl | $OCH_3$ | $OCH_3$ | white crystal | 238–240 |
| 65 | CH | O | H | H | Cl | H | $OCH_3$ | $OCH_3$ | white crystal | 209–211 |
| 66 | CH | O | 6-Br | H | Cl | Cl | F | F | white crystal | 230–233 |
| 67 | CH | O | 6-Br | H | Cl | Cl | Cl | H | white crystal | 210–213 |
| 68 | CH | O | 6-Br | H | Cl | Cl | Cl | Cl | white crystal | 271–274 |

Preparation of compounds represented by the following formula Ib:

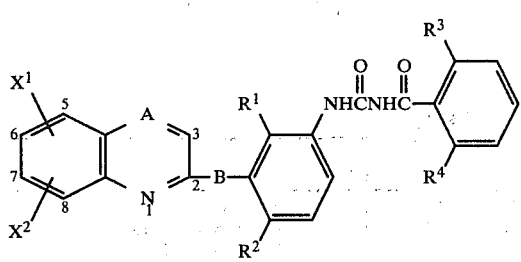

TABLE 2

| Compound No | A | B | $X^1$ | $X^2$ | $R^1$ | $R^2$ | $R^3$ | $R^4$ | Properties | m.p. (°C.) |
|---|---|---|---|---|---|---|---|---|---|---|
| 69 | N | O | 6-Cl | H | H | H | Cl | H | white crystal | 219–221 |
| 70 | N | O | 6-Cl | H | H | H | Cl | Cl | white crystal | 190–192 |
| 71 | N | O | H | H | H | H | F | F | white crystal | 203–205 |
| 72 | N | O | H | H | H | H | F | Cl | white crystal | 195–197 |
| 73 | N | O | H | H | H | H | Cl | H | white crystal | 196–197 |
| 74 | N | O | H | H | H | H | Cl | Cl | white crystal | 190–192 |
| 75 | N | O | H | H | H | H | $OCH_3$ | $OCH_3$ | white crystal | 182–184 |
| 76 | N | O | 6-F | H | H | H | F | F | white crystal | 200–201.5 |
| 77 | N | O | 6-F | H | H | H | F | Cl | white crystal | 171–173 |
| 78 | N | O | 6-F | H | H | H | Cl | H | white crystal | 215–216 |
| 79 | N | O | 6-F | H | H | H | Cl | Cl | white crystal | 189–192 |
| 80 | N | O | 6-F | H | H | H | $OCH_3$ | $OCH_3$ | white crystal | 217–218 |
| 81 | N | S | 6-F | H | H | H | F | F | white crystal | 219–221 |
| 82 | N | S | 6-F | H | H | H | F | Cl | white crystal | 163–165 |
| 83 | N | S | 6-F | H | H | H | Cl | H | white crystal | 210–212 |
| 84 | N | S | 6-F | H | H | H | Cl | Cl | white crystal | 191–193 |
| 85 | N | S | 6-F | H | H | H | $OCH_3$ | $OCH_3$ | white crystal | 202–205 |
| 86 | N | O | 6-Cl | H | H | H | F | F | white crystal | 198–201 |
| 87 | N | O | 6-Cl | H | H | H | F | Cl | white crystal | 178–180 |
| 88 | N | O | 6-Cl | H | H | H | $OCH_3$ | $OCH_3$ | white crystal | 195–198 |
| 89 | N | O | 6-Cl | H | H | Cl | F | F | white crystal | 235–237 |
| 90 | N | O | 6-Cl | H | H | Cl | F | Cl | white crystal | 193–195 |
| 91 | N | O | 6-Cl | H | H | Cl | Cl | H | white crystal | 210–212 |
| 92 | N | O | 6-Cl | H | H | Cl | Cl | Cl | white crystal | 204–206 |
| 93 | N | O | 6-Cl | H | H | Cl | $OCH_3$ | $OCH_3$ | white crystal | 208–210 |
| 94 | N | O | 6-Br | H | H | H | F | Cl | white crystal | 188–190 |
| 95 | N | O | 6-$CF_3$ | H | H | H | F | F | white crystal | 199–201 |
| 96 | N | O | 6-$CF_3$ | H | H | H | F | Cl | white crystal | 186–188 |
| 97 | N | O | 6-$CF_3$ | H | H | H | Cl | Cl | white crystal | 192–194 |
| 98 | CH | O | H | H | H | H | F | F | white crystal | 156–158 |
| 99 | CH | O | H | H | H | H | F | Cl | white crystal | 161–163 |
| 100 | CH | O | H | H | H | H | Cl | H | white crystal | 180–182 |
| 101 | CH | O | H | H | H | H | Cl | Cl | white crystal | 180–182 |
| 102 | CH | O | H | H | H | H | $OCH_3$ | $OCH_3$ | white crystal | 202–205 |
| 103 | CH | O | 6-Br | H | H | H | F | F | white crystal | 202–203 |
| 104 | CH | O | 6-Br | H | H | H | F | Cl | white crystal | 219–220 |
| 105 | CH | O | 6-Br | H | H | H | Cl | H | white crystal | 203–204 |

Next, formulation examples of insecticides containing the compounds of this invention are illustrated below. In these examples, parts are by weight.

| Formulation 1 | Emulsifiable concentrate: |
|---|---|
| compound of this invention | 5 parts |
| xylol | 80 parts |
| Sorpol 2680 (a product of Toho Chem. Industrial Co., Ltd.) | 15 parts |

The above ingredients are uniformly mixed to obtain an emulsifiable concentrate. This emulsifiable concentrate is diluted with water to 50 times, and sprayed in a quantity of 25–50 ml/m² or diluted with water to 1,000–2,000 times and sprayed in a quantity of 100–150 1/10 a.

| Formulation 2 | oil-form: |
|---|---|
| compound of this invention | 0.1 part |
| piperonyl butoxide | 0.9 part |
| white kerosene | 99.0 parts |

The above ingredients are uniformly mixed to form an oil. This oil is applied in a quantity of 25–50 ml/m² to ditches or pools.

| Formulation 3 wettable powder form: | |
|---|---|
| compound of this invention | 10 parts |
| Siegreit (a product of Siegreit Mining Co.) | 75 parts |
| Carplex (a product of Shionogi & Co. Ltd.) | 10 parts |
| Sorpol 8048 (a product of Toho Chem. Industrial Co., Ltd.) | 3 parts |
| Runox 1000 (the same as above) | 2 parts |

The above ingredients are uniformly mixed and ground to obtain a wettable powder. In use, the wettable powder is diluted with water to 500–2,000 times, and sprinkled in a quantity of 50–500 1/10 a.

| Formulation 4 dust-form: | |
|---|---|
| compound of this invention | 0.4 part |
| piperonyl butoxide | 1.6 parts |
| talc | 98 parts |

The above ingredients are uniformly mixed to obtain a dust. This dust is scattered in a quantity of 15 g/m² or 3–4 Kg/10 a.

| Formulation 5 granular form: | |
|---|---|
| compound of this invention | 5 parts |
| bentonite | 95 parts |

The above ingredients are uniformly mixed and ground. After addition of a small amount of water, the resulting mixture is thoroughly mixed, pelletized through an extrusion type pelletizer and dried to obtain granules. The granules are scattered as such, in a quantity of 3–4 Kg/10 a.

Next, excellent insecticidal action of the compounds of this invention is illustrated with reference to tests which are compared with controls using a commercially available product (diflubenzuron) represented by the following formula:

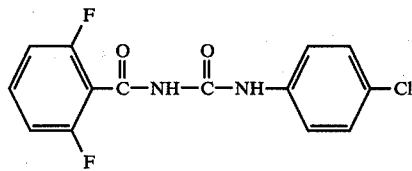

Test 1 killing test to Tobacco cutworm larvae:

Cabbage leaf pieces were immersed for about 10 sec. in a solution prepared by dispersing an active ingredient component compound into water and adjusting the concentration to a predetermined level. The cabbage leaf pieces were then picked up, dried in air and placed on a moistened filter paper in a Petri dish, 9 cm in diameter. Tobacco cutworm second instar larvae were set on the pieces, and after closing the dish with the cover, it was kept within a constant-temperature room at 25° C. equipped with lights. Seven days after setting the larvae, the mortality was checked. The mortality was determined according to the formula:

$$\text{Mortality} = \frac{\text{number of larvae killed}}{\text{number of larvae set}} \times 100$$

The results are shown in Table 3.

TABLE 3

| Tested Compound (compound No.) | Mortality Concen. of effective ingredient compound | |
|---|---|---|
| | 10 ppm | 1 ppm |
| control compound (diflubenzuron) | 90 | 20 |
| 4 | 100 | 100 |
| 6 | 80 | 30 |
| 7 | 100 | 100 |
| 9 | 100 | 80 |
| 11 | 100 | 100 |
| 12 | 100 | 100 |
| 14 | 100 | 100 |
| 15 | 100 | 100 |
| 16 | 90 | 60 |
| 17 | 100 | 70 |
| 18 | 100 | 50 |
| 19 | 80 | 40 |
| 20 | 100 | 100 |
| 22 | 100 | 100 |
| 23 | 100 | 100 |
| 24 | 100 | 100 |
| 25 | 100 | 100 |
| 28 | 60 | 30 |
| 29 | 100 | 100 |
| 30 | 100 | 50 |
| 33 | 100 | 80 |
| 35 | 100 | 100 |
| 70 | 100 | 100 |
| 36 | 100 | 45 |
| 38 | 100 | 100 |
| 39 | 100 | 100 |
| 40 | 80 | 10 |
| 43 | 100 | 100 |
| 45 | 100 | 100 |
| 51 | 100 | 100 |
| 52 | 100 | 70 |
| 54 | 100 | 100 |
| 55 | 100 | 100 |
| 57 | 100 | 100 |
| 58 | 100 | 50 |
| 59 | 100 | 35 |
| 62 | 100 | 100 |
| 63 | 100 | 100 |
| 66 | 100 | 100 |
| 67 | 100 | 100 |
| 68 | 100 | 85 |
| 76 | 100 | 95 |
| 77 | 100 | 100 |
| 79 | 100 | 80 |
| 82 | 100 | 100 |
| 83 | 90 | 25 |
| 84 | 100 | 100 |
| 86 | 100 | 100 |
| 87 | 100 | 100 |
| 89 | 100 | 50 |
| 90 | 100 | 100 |
| 91 | 100 | 100 |
| 92 | 100 | 40 |
| 94 | 100 | 100 |
| 95 | 100 | 100 |
| 96 | 100 | 100 |
| 97 | 100 | 100 |
| 99 | 100 | 70 |
| 103 | 100 | 100 |
| 104 | 100 | 100 |
| 105 | 100 | 100 |

Test 2 killing test for diamondback moth larvae

In the same manner as in Test 1, a wet filter paper was placed in a Petri dish. Cabbage leaf pieces treated with an agent solution were placed on the moistened filter paper and dried in air. Then, diamondback moth second instar larvae were set on the pieces. In the same manner as in Test 1, the % kill was determined seven days after setting the larvae. The results are shown in Table 4.

TABLE 4

| Tested Compound (compound No.) | Mortality Concen. of effective ingredient compound | |
|---|---|---|
| | 1000 ppm | 200 ppm |
| control compound (diflubenzuron) | 100 | 20 |
| 1 | 100 | 40 |
| 2 | 70 | 30 |
| 3 | 50 | 30 |
| 4 | 100 | 100 |
| 6 | 70 | 40 |
| 7 | 100 | 100 |
| 8 | 100 | 70 |
| 9 | 100 | 100 |
| 10 | 100 | 50 |
| 11 | 100 | 100 |
| 12 | 100 | 50 |
| 14 | 100 | 100 |
| 15 | 100 | 100 |
| 16 | 100 | 90 |
| 17 | 100 | 100 |
| 18 | 100 | 100 |
| 19 | 100 | 80 |
| 20 | 100 | 100 |
| 21 | 70 | 30 |
| 22 | 100 | 100 |
| 23 | 100 | 100 |
| 24 | 100 | 100 |
| 25 | 100 | 100 |
| 27 | 80 | 40 |
| 29 | 100 | 100 |
| 30 | 100 | 100 |
| 31 | 100 | 80 |
| 33 | 100 | 100 |
| 34 | 90 | 30 |
| 35 | 100 | 100 |
| 70 | 100 | 100 |
| 36 | 100 | 50 |
| 38 | 100 | 90 |
| 39 | 100 | 80 |
| 40 | 100 | 100 |
| 43 | 100 | 65 |
| 45 | 100 | 70 |
| 51 | 100 | 85 |
| 52 | 100 | 45 |
| 54 | 100 | 85 |
| 55 | 100 | 90 |
| 57 | 100 | 90 |
| 58 | 100 | 55 |
| 59 | 100 | 60 |
| 62 | 100 | 100 |
| 63 | 100 | 100 |
| 66 | 100 | 100 |
| 67 | 100 | 100 |
| 68 | 100 | 95 |
| 76 | 100 | 100 |
| 77 | 100 | 100 |
| 79 | 100 | 60 |
| 82 | 100 | 75 |
| 83 | 100 | 95 |
| 84 | 100 | 45 |
| 86 | 100 | 100 |
| 87 | 100 | 100 |
| 89 | 100 | 100 |
| 90 | 100 | 100 |
| 91 | 100 | 100 |
| 92 | 100 | 100 |
| 94 | 100 | 100 |
| 95 | 100 | 100 |
| 96 | 100 | 100 |
| 97 | 100 | 95 |
| 99 | 100 | 35 |
| 103 | 100 | 100 |
| 104 | 100 | 100 |
| 105 | 100 | 80 |

Test 3 Killing test to twenty-eight-spotted lady beetle larvae:

In the same manner as in Test 1, a wet filter paper was placed in a petri dish. Tomato leaf pieces treated with an agent solution were placed on the moistened filter paper and dried in air. Then, second instar larvae were set on the pieces. In the same manner as in Test 1, the % kill was determined seven days after setting the larvae. The results are shown in Table 5.

TABLE 5

| Tested Compound (compound No.) | Mortality Concen. of effective ingredient compound |
|---|---|
| | 30 ppm |
| control compound (diflubenzuron) | 100 |
| 49 | 100 |
| 53 | 100 |
| 98 | 100 |
| 100 | 100 |
| 101 | 100 |

What is claimed is:

1. A heterocyclic ether or thioether linkage containing urea compound of the formula I:

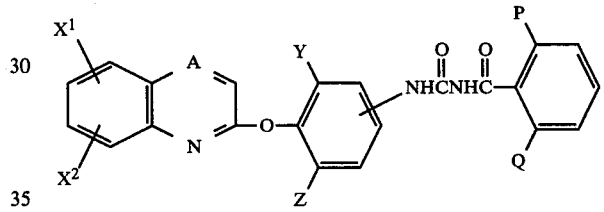

wherein A denotes nitrogen, $X^1$ and $X^2$ denote independently of each other hydrogen, halogen or trifluoromethyl, Y and Z denote independently of each other hydrogen or chlorine, and P and Q denote independently of each other hydrogen or halogen.

2. The heterocyclic ether or thioether linkage containing urea compound claimed in claim 1, having the formula:

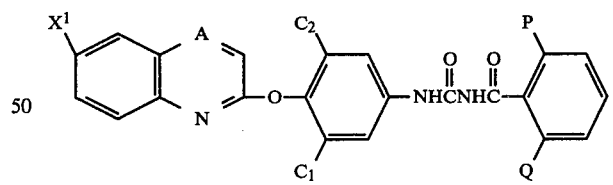

wherein A, $X^1$ and Q have the same meanings given in claim 1 respectively and P denotes halogen.

3. The heterocyclic ether or thioether linkage containing urea compound claimed in claim 1, having the formula:

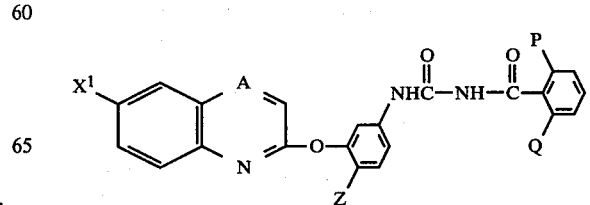

wherein $X^1$ denotes hydrogen, halogen or trifluoromethyl group, P and Q denote independently of each other hydrogen or halogen, and A and Z denote the same meanings given in claim 1.

4. The heterocyclic ether or thioether linkage containing urea compound of claim 1, having the formula:

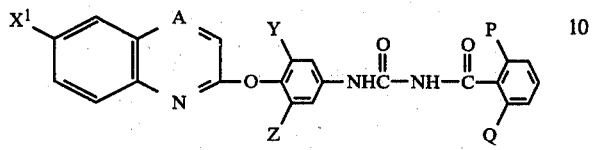

wherein $X^1$ is hydrogen or halogen, Y and Z denote chlorine, P and Q denote halogen, and A denotes the same meanings given in claim 1.

5. The heterocyclic ether or thioether linkage containing urea compound of claim 4, having the formula:

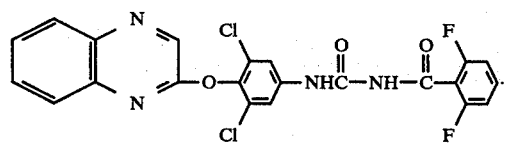

6. The heterocyclic ether or thioether linkage containing urea compound of claim 4, having the formula:

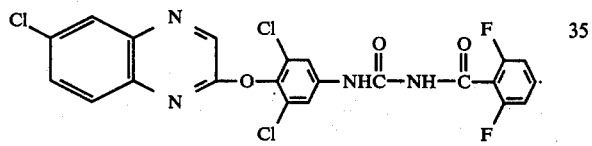

7. The heterocyclic ether or thioether linkage containing urea compound of claim 4, having the formula:

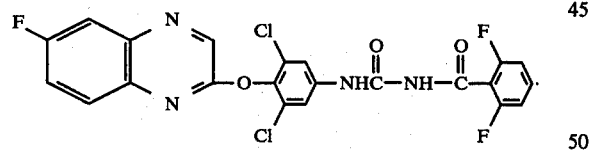

8. A method for controlling insects, comprising administering an insecticidally effective amount of a compound having the formula:

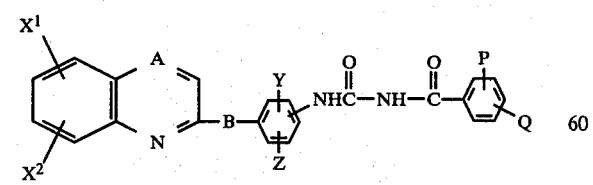

wherein B denotes oxygen or sulfur, A denotes nitrogen, $X^1$ and $X^2$ denote independently of each other hydrogen, halogen trifluoromethyl group or nitro group, Y and Z denote independently of each other hydrogen atom or halogen, and P and Q denote independently of each other hydrogen halogen, alkoxyl group or alkyl group.

9. The heterocyclic ether or thioether linkage containing urea compound as claimed in claim 3, wherein A, $X^1$, Z and Q have the same meaning as in claim 3 and P denotes halogen.

10. The heterocyclic ether or thioether linkage containing urea compound of claim 3, having the formula:

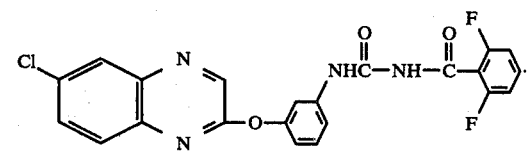

11. The heterocyclic ether or thioether linkage containing urea compound of claim 3, having the formula:

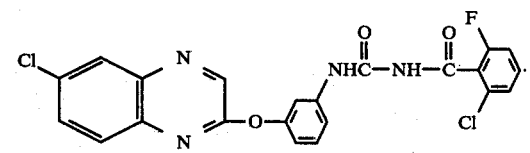

12. The heterocyclic ether or thioether linkage containing urea compound of claim 3, having the formula:

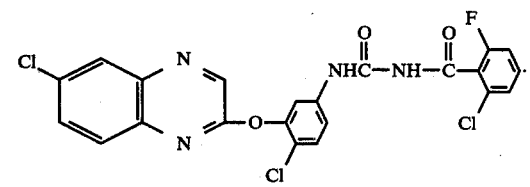

13. The heterocyclic ether or thioether linkage containing urea compound of claim 3, having the formula:

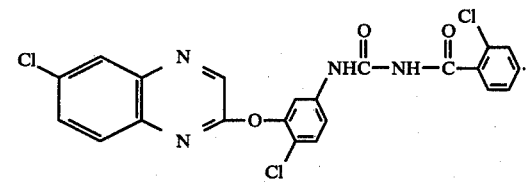

14. The heterocyclic ether or thioether linkage containing urea compound of claim 3, having the formula:

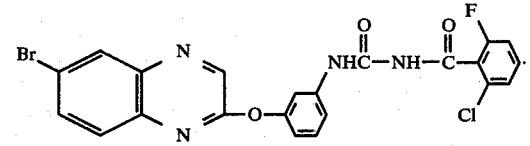

15. The heterocyclic ether or thioether linkage containing urea compound of claim 3, having the formula:

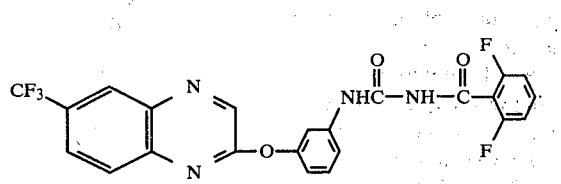

16. The heterocyclic ether or thioether linkage containing urea compound of claim 3, having the formula:

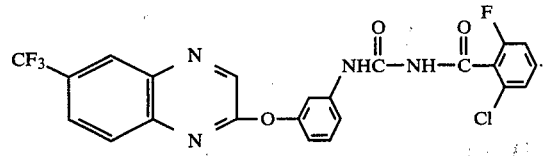

17. The heterocyclic ether or thioether linkage containing urea compound of claim 3, having the formula:

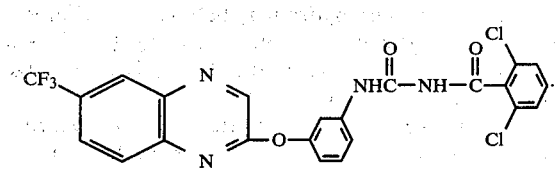

18. An insecticidal composition which comprises an insecticidally effective amount of a compound of a heterocyclic ether or thioether linkage containing urea compound of the formula I according to claim 1, and an argicultural adjuvant in a form of a solution, a dispersion, an emulsifiable concentrate, an oil spray, a wettable powder, a dust, a granule, a tablet, a pellet, a paste or an aerosol.

19. The insecticidal composition according to claim 18, which further comprises piperonyl butoxide, octachlorodipropyl ether or N-octyl bicycloheptane dicarboxyimide.

20. The insecticidal composition according to claim 18, which further comprises an antioxidant.

* * * * *